United States Patent
Mauderli et al.

(10) Patent No.: US 6,637,372 B2
(45) Date of Patent: Oct. 28, 2003

(54) APPARATUS AND METHODS FOR TESTING PAIN SENSITIVITY

(75) Inventors: Andre Paul Mauderli, Dunnellon, FL (US); Charles J. Vierck, Gainesville, FL (US)

(73) Assignee: Unversity of Florida, Gainesville, FL (US)

( * ) Notice: Subject to any disclaimer, the term of this patent is extended or adjusted under 35 U.S.C. 154(b) by 0 days.

(21) Appl. No.: 10/313,636

(22) Filed: Dec. 5, 2002

(65) Prior Publication Data

US 2003/0150395 A1 Aug. 14, 2003

Related U.S. Application Data

(63) Continuation-in-part of application No. 10/004,662, filed on Dec. 5, 2001.

(51) Int. Cl.$^7$ ................................................. A01K 29/00
(52) U.S. Cl. ........................................ 119/417; 119/421
(58) Field of Search ................................ 119/417, 418, 119/421, 712, 719, 720, 721

(56) References Cited

U.S. PATENT DOCUMENTS

| | | | | |
|---|---|---|---|---|
| 2,244,082 A | * | 6/1941 | Reyniers | 600/21 |
| 3,693,590 A | * | 9/1972 | Bowers | 119/421 |
| 4,337,726 A | * | 7/1982 | Czekajewski et al. | 119/421 |
| 4,574,734 A | * | 3/1986 | Mandalaywala et al. | 119/421 |
| 4,968,974 A | * | 11/1990 | Sakano | 340/573.3 |
| 5,608,209 A | * | 3/1997 | Matsuda | 250/221 |
| 5,721,207 A | * | 2/1998 | Noble et al. | 514/9 |
| 5,915,332 A | * | 6/1999 | Young et al. | 119/421 |
| 6,062,224 A | * | 5/2000 | Kissinger et al. | 128/897 |
| 6,223,690 B1 | * | 5/2001 | Park | 119/248 |
| 6,273,026 B1 | * | 8/2001 | Ferster et al. | 119/421 |
| 6,345,943 B1 | * | 2/2002 | Lawson et al. | 410/29.1 |
| 2003/0024482 A1 | * | 2/2003 | Gondhalekar et al. | 119/417 |

OTHER PUBLICATIONS

Bohus, B. and D. Wied "Avoidance and escape behavior following medial thalamic lesions in rats" *J Comp Physiol Psychol* [1967] 64(1):26–29.

Chaplan, S.R. et al. "Quantitative assessment of tactile allodynia in the rat paw" *J Neurosci Methods* [1994] 53:55–63.

Chapman, C.R et al. "Pain Measurement—an Overview" *Pain* [1985] 22:1–31.

Cleary, A. *Instrumentation for Psychology* [1977] pp. 131–222.

D'Amour, F.E. and D. Smith "A method for determining loss of pain sensation" *J Pharmacol Exp Ther* [1941] 72:74–79.

Dubner, R. "Methods of assessing pain in animals" *Textbook of Pain* [1989], pp. 247–256.

Dubuisson, D and S.G. Dennis "The formalin test: a quantitative study of the analgesic effects of morphine, meperidine, and brain stem stimulation in rats and cats" *Pain* [1977] 4:161–174.

Hargreaves, K et al. "A new and sensitive method for measuring thermal nociception in cutaneous hyperalgesia" *Pain* [1988] 32:77–88.

(List continued on next page.)

*Primary Examiner*—Yvonne Abbott
(74) *Attorney, Agent, or Firm*—Saliwanchik, Lloyd & Saliwanchik

(57) ABSTRACT

The subject invention concerns an apparatus for testing pain sensitivity in an animal. The apparatus can be used to evaluate pain sensitivity in response to a disease state, drug, surgical procedure, or other intervention. The subject invention also pertains to methods for testing pain sensitivity in an animal, using the apparatus. The apparatus of the subject invention can be automated and used in conjunction with software for control of experimental conditions, response measurements, and data analysis.

82 Claims, 2 Drawing Sheets

OTHER PUBLICATIONS

Mauderli, A.P. et al. "An operant assay of thermal pain in conscious, unrestrained rats" *J Neurosci Methods* [2000] 97:19–29.

McGrath, P.A. et al. "Masseter inhibitory periods and sensations evoked by electrical tooth pulp stimulation" *Pain* [1981] 10:1–17.

Randall, P.K. and D.C. Riccio "Fear and punishment as determinants of passive–avoidance responding" *J Comp Physiol Psychol* [1969] 69(3):550–553.

Sandkuhler, J. and G.F. Gebhart "Characterization of inhibition of a spinal nociceptive reflex by stimulation medially and laterally in the midbrain and medulla in the pentobarbital–anesthetized rat" *Brain Res* [1984] 305:67–76.

Vierck, C.J. et al. "Behavioral analysis of CNS pathways and transmitter systems involved in conduction and inhibition of pain sensation and reactions in primates" *Progress in Psychobiology and Physiological Psychology* [1983] pp. 113–165.

Vierck, C.J. and B.Y. Cooper, "Guidelines for assessing pain reactions and pain modulation in laboratory animal subjects" *Advances in Pain Research and Therapy* [1984], pp. 305–322.

Vierck, C.J. et al. "Inference of pain sensitivity from complex behaviors of laboratory animals" *Issues in Pain Measurement* [1989] pp. 93–115.

Willer, J.C. et al. "Supraspinal influences on nociceptive flexion reflex and pain sensation in man" *Brain Res* [1979] 179:61–68.

Woolfe, G and A.D. MacDonald, "The evaluation of the analgesic action of pethidine hydrochloride (Demerol)" *J Pharmacol Exp Ther* [1944] 80:300–307.

\* cited by examiner

APPARATUS AND METHODS FOR TESTING PAIN SENSITIVITY

CROSS-REFERENCE TO RELATED APPLICATIONS

The present application is a continuation-in-part of U.S. application Ser. No. 10/004,662, filed Dec. 5, 2001, which is hereby incorporated by reference herein in its entirety, including any figures, tables, or drawings.

The subject invention was made with government support under a research project supported by National Institutes of Health Grant Nos. RO1 NS07261, T32 DE07200, and K15 DE00375. The government has certain rights in this invention.

BACKGROUND OF THE INVENTION

The broad definition of pain includes neural processes that take place to identify internal or external environmental influences that pose a risk for tissues of the body. Neural systems first calculate the magnitude of the risk. Depending on this magnitude, the systems will generate the driving force for a battery of behaviors aimed at minimizing the risk of tissue damage. For localized high intensity stimuli (such as when a hot stove is touched) speed of the response is of highest priority. There is no time for an in-depth analysis of all aspects of the threat, and information about location and intensity of the stimulus dominate the process that leads to a stereotypical but rapid first response (reflex withdrawal). For lower intensity or diffuse stimuli, or for stimuli where reflexes have failed to bring the desired result, higher-order neural circuitry is recruited for an in-depth analysis of the threat and generation of a response adapted to the specific situation. The signal that arrives from the site of tissue insult will be temporally and spatially integrated because the risk (and thus urgency of response) is a function of intensity x duration x spatial extent of the stimulus. The experiential and behavioral result of this computation may be subject to modification to better adapt the response to situational factors that are important for the survival of the animal as a whole. For instance, surviving a fight or flight situation takes precedence over protecting an injured paw, and thus pain from the paw will be suppressed until the animal has reached a safer environment.

The clinical definition of pain relates to the net result of many steps of neural processing. Typically, the definition is limited to the input side of the phenomenon of pain, namely the conscious experiential aspects. The output stage (escape, vocalization, verbal response) is often not included in the narrow definition of pain, but merely considered a means to infer the magnitude of the sensory or affective experience. Conscious (clinically most relevant) aspects of pain are the result of many more steps of neural processing than simple withdrawal reflexes. Clinical pain may be generated under conditions that do not lead to activation or facilitation of reflexes. Furthermore, suppression of protective reflexes is not an objective of pain medicine and may not be in the interest of the patient at all. The goal is reduction of the conscious unpleasant, often persistent experience of pain. Animal models, to be clinically relevant, must be predictors of this conscious pain experience.

Pain is an experience that cannot be measured directly, either in humans, or in animals, but must be inferred from behaviors. The available repertoire of behaviors that consistently reveal pain includes verbalizations in humans and complex motor sequences that eliminate nociceptive stimulation (escape responses) in humans and other animals. A variety of other behaviors suggest the presence of pain but can be elicited by stimuli or situations that are not necessarily aversive or involve responses that do not require a conscious perception of pain. Pain tests for non-human animals have been reviewed extensively in the literature (Vierck, C. J., B. Y. Cooper, *Advances in Pain Research and Therapy* [1984], pp. 305–322; Chapman, C. R et al., *Pain* [ 1985] 22:1–31; Dubner, R. *Textbook of Pain* [ 1989], pp. 247–256; Franklin, K. B. J and F. V. Abbott, *Neuromethods, Psychopharmacology* [1989] 13:145–215; Vierck, C. J. et al., *Issues in Pain Measurement* [1989] pp. 93–115), and they can be classified according to two main criteria: (I) type of stimulus applied; and (2) type of response measured.

Some methods for evaluating phasic responses to nociceptive stimulation involve electrical stimulation, because it can be turned on and off instantly, making it easy for an animal to learn the temporal relationship between an escape response and elimination of an aversive sensation. Although electrical stimulation has been criticized because skin receptors are bypassed, and synchronous afferent firing patterns are generated (Dubner, R., 1989), it is possible to elicit natural sensations of predictable quality when electrode tissue coupling is tightly controlled (Vierck, C. J. et al., *Animal Pain Perception and Alleviation; American Physiological Society* [1983a] pp. 117–132; Vierck, C. J. et al., 1989; Vierck, C. J. et al., *Somatosens Mot Res* [1995] 12:163–174). However, control over current density and stimulus location can be achieved only by restraining the subjects, and animals will tolerate restraint only after lengthy adaptation and training periods. Restraint without proper adaptation leads to high levels of stress and anxiety—factors that are known to have modulatory effects on pain sensitivity (Amir, S. and Z. Amit, *Life Sci* [1978 ] 23:1143–1151; Bhattacharya, S. K. et al., *Eur J Pharmacol* [1978] 50:83–85; Basbaum, A. I. and H. L. Fields, *Annu Rev Neurosci* [1984] 7:309–338; Franklin, K. B. J. and F. V. Abbott, 1989; Maier, S. F. et al., *APS J* [1992] 1:191–198; Tokuyama, S. et al., *Jpn J Pharmacol* [1993] 61:237–242; Caceres, C. and J. W. Burns, *Pain* [1997] 69:237–244). Therefore, nociceptive tests that require restraint or extensive handling, which have an effect on pain processing, may produce contaminated results.

Thermal stimulation has been used previously for nociceptive tests (Dubner, R., 1989). Contact thermal stimulation provides the basis for the hotplate test (Woolfe, G and A. D. Macdonald, *J Pharmacol Exp Ther* [1944] 80:300–307), and extensive use of contact heat in psychophysical and neurophysiological studies has established the range of temperatures that produces heat nociception. Radiant heat is used in the tailflick test (D'Amour, F. E. and D. Smith, *J Pharmacol Exp Ther* [1941] 72:74–79) and the Hargreaves hindlimb-withdrawal test (Hargreaves, K et al., *Pain* [1988] 32:77–88). The absence of a concurrent mechanical stimulus is thought to be an advantage of radiant heat, but it is difficult to control and assess skin temperature. Observations of hindlimb withdrawal and/or guarding behavior have also been utilized to evaluate thresholds for reactivity to mechanical stimulation (Chaplan, S. R. et al. *J Neurosci Methods* [1994] 53:55–63) or the frequency of responsivity to chemical stimulation (Dubuisson, D and S. G. Dennis, *Pain* [1977] 4:161–174). A present difficulty with mechanical tests is that characteristics of von Frey filaments (e.g. combinations of diameter and force) which produce mechanical nociception have not been determined. Chemical stimuli can be varied in concentration, volume and method of application (injection or surface application), but it is difficult to characterize the effects of these agents on peripheral tissues, receptors and afferents. These different methods of nociceptive testing elicit responses that can be modulated differentially by a variety of treatments (Willer, J. C. et al. *Brain Res* [1979] 179:61–68; McGrath, P. A. et al., *Pain* [1981] 10:1–17; Vierck, C. J. et al., *Progress in Psychobiology and Physiological Psychology* [ 1983] pp. 113–165; Sandkuhler, J. and G. F. Gebhart, *Brain Res* [1984] 305:67–76; Dubner, R., 1989), and it is often concluded that the method of stimulation is the determinant factor, without consideration of other aspects of the testing method and response measurement.

An important consideration in evaluation of nociceptive tests is the central circuitry that is interposed between the input and output stages. For example, the tail flick and paw withdrawal responses can be elicited in spinal animals (Franklin, K. B. J. and F. V. Abbott, 1989) and therefore can represent segmental spinal reflexes. Pawlicking in the hot-plate test (Woolfe, G. and A. D. Macdonald, 1944; Eddy, N. B. et al., *J Pharmacol Exp Ther* [1950] 98:121–137; Chapman, C. R et al., 1985) and vocalization (Carroll, M. N and R. K. S. Lim, *Arch Int Pharmacodyn* [1960] 125:383–403) can be elicited in chronic decerebrate rats (Woolf, C. J., *Pain* [1984] 18:325–343; Berridge, K. C., *Behav Brain Res* [1989] 33:241–253; Matthies, B. K. and K. B. Franklin, *Pain* [1992] 51:199–206) and can be modulated differentially from responses to the same stimulus that originate at higher levels of the neuraxis (Sandkuhler, J. and G. F. Gebhart, 1984; Cooper, B. Y. and C. J. Vierck, *Pain* [1986] 26:393–407; Dubner, R., 1989). Therefore, it is important to distinguish innate responses that can be segmental (spinal) reflexes or long-loop (spino-bulbospinal) reflexes from operant responses that necessarily employ complex learned motor actions (involving the cerebrum).

Animal models of pain are most useful when they are good predictors of the effect of disease states or therapeutic interventions on human clinical pain. The clinically most relevant consequence of nociceptive stimuli is the conscious experience of pain and suffering that the stimuli may elicit. Assays based upon short or long-loop reflexes (such as the tail-flick test, paw withdrawal test, or hotplate test) provide little or no insight into what goes on at the conscious level. Reflex tests and the few available assays of conscious responses to painful stimuli, such as the foot shock escape test, rely mostly on fast-conducting pain pathways. However, it is known that slow-conducting nociceptive systems are the major contributors to the conscious experience of clinical pain and they are primarily affected by powerful pain killers such as morphine.

Shuttle-box paradigms, using the operant response measure of learned escape have been popular models of conscious aspects of pain (Warner, L. H., *J Genetic Psychol* [1932] 41:57–89; Bohus, B. and D. Wied, *J Comp Physiol Psychol* [1967] 64:26–29; Randall, P. K. and D. C. Riccio, *J Comp Physiol Psychol* [1969] 69:550–553; Cleary, A. *Instrumentation for Psychology* [1977] pp. 1–319). These methods are easy to implement, because the subjects are unrestrained. Electrical stimulation has been used in shuttle box paradigms because it can be regulated in intensity and switched between chambers. However, it is problematic in these situations, because movement of the animals across a grid floor switches polarities and varies current densities.

A shuttle-box test was developed which uses thermal nociceptive stimulation (hot or cold), as opposed to electrical stimulation (Mauderli, A. P. et al., *J Neurosci Methods* [2000] 97:19–29). The thermal stimulus is transmitted from a thermal plate on the floor of a compartment to the paws of the freely moving animals. However, through training, the animals learn that they can escape the stimulus by moving from the heated compartment, which is kept dark, onto a non-heated platform within an enclosure, which is suspended within the heated compartment. Thus, the enclosed platform represents the destination for escape from the thermal plate. However, to discourage avoidance behavior, the escape platform is made less attractive by brightly illuminating it and imposing a degree of tilt toward the dark compartment. The thermal plate is kept constantly heated by internal water circulation and a new trial is started by swinging the enclosure into a vertical position, thereby ejecting the animal onto the thermal plate.

Tests of nociception are most often used to evaluate pharmacological, disease, or surgical effects on pain. However, these effectors may alter the measured behaviors through mechanisms other than pain. Morphine, for instance, may make the animal sluggish in response to any stimulus, including non-painful stimuli. Therefore, it is necessary to pair any pain test with a valid control test for non-pain-related effects, such as attentional, motivational and motor effects (Dubner, R., 1989). To be valid, treatment effects on escape should be compared with effects on a control task that involves a comparable motivation (escape) and the same motor response (e.g. stepping on a platform) as the nociceptive test. The rotarod test (Dunham, N. W. and T. S. Miya, *J Am Pharm Assoc* [1957] 46:208–209; Kinnard Jr., W. J. and C. J. Carr, *J Pharmacol Exp Ther* [1957] 121:354–361) for instance, cannot be considered an adequate control for a reflex-based test or an operant shuttle-box assay of nociception, because the motor tasks and motivations differ considerably for these tests.

A control test for the thermal escape test was developed (Mauderli, A. P. et al., 2000), which measures latencies for escape from a bright light (controlling for generalized effects on aversion). In this arrangement, a two-chambered box that uses only bright light as the behavioral driving force is utilized for motor and general motivational effects for the thermal pain test. which is conducted in a separate apparatus. Therefore, the motor task in the control test is similar to that required by the thermal escape test, in that both involve escape into another compartment and use of a bright light. However, there are differences in the apparatuses used in the control test and thermal escape test that may limit their effectiveness. The differences in design between the two apparatuses requires that each animal be trained on both tasks and be able to distinguish between them. In addition, responses in the thermal escape test are always directed toward the same compartment (a one-way shuttle test), but the control test is a two-way test, because the aversive light can occur in either of the two chambers. A one-way shuttle test carries the risk that the animal can learn to associate between "comfort" and a specific compartment or location. In addition, for experimental treatments that influence memory, it can be a drawback if the difficulty level of the two tests is not the same.

It is evident that the behavioral testing devices currently available may be of limited use as research tools with respect to nociception. Accordingly, there remains a need for a device which is capable of testing pain based upon a conscious response, permits assessment of slowly-conducting pain systems, avoids restraint stress, minimizes animal handling artifacts, and is matched with a valid behavioral and motor control test.

BRIEF SUMMARY OF THE INVENTION

The subject invention concerns an apparatus for testing pain sensitivity exhibited by an animal. The apparatus can be used, for example, to evaluate the effect of a disease state, drug, or other intervention, on pain sensitivity. The apparatus is designed to measure a conscious escape response to a painful stimulus in test animals, such as rodents. The apparatus of the subject invention provides an inclusive operant pain test and a matching motor control test. The subject invention also pertains to methods for testing the pain sensitivity exhibited by a test animal, using the subject apparatus.

In a preferred embodiment, the apparatus of the subject invention includes two chambers, a first chamber and a second chamber, which are connected by a passageway. The passageway is of sufficient size to permit the test animal to pass between the chambers. Preferably, the passageway is designed such that the test animal can pass through the passageway even if the test animal is tethered to infusion cannula(s), cable(s), or other diagnostic and/or delivery device(s). The subject invention also includes single chamber embodiments.

Optionally, wireless telemetry can be utilized to transmit and receive diagnostic information (e.g., biological information) concerning the test animal. Wireless telemetry systems include, for example, radio-electric transmission, optical transmission, ultrasound transmission, or other transmission technologies that do not rely on a continuous wire, lead, or cable connection between the test animal and any external equipment.

The apparatus also includes means for presenting a painful stimulus to the test animal when the test animal is within the first chamber and a means for presenting a painful stimulus to the test animal when the test animal is within the second chamber. The means for presenting a painful stimulus presents a stimulus that is aversive and at least potentially painful to the test animal within the chamber where the means for presenting the painful stimulus is activated and in which the painful stimulus is produced. Preferably, the painful stimulus can motivate the test animal to exhibit an escape response, such as exiting the chamber in which the painful stimulus is presented.

Preferably, the means for presenting a painful stimulus to the test animal when the test animal is within the first chamber produces a painful condition (environment) within the first chamber. Preferably, the means for presenting a painful stimulus to the test animal when the test animal is within the second chamber produces a painful condition (environment) within the second chamber. Each means for presenting a painful stimulus can be independently activated and deactivated. Each painful stimulus can be independently and rapidly presented and independently and rapidly removed.

The apparatus further includes means for presenting an aversive, non-painful stimulus to the test animal when the test animal is within the first chamber and a means for presenting an aversive, non-painful stimulus to the test animal when the test animal is within the second chamber. The means for presenting an aversive, non-painful stimulus when the test animal is within the first and second chamber can each motivate the test animal to exhibit an escape response, such as exiting the chamber in which the aversive, non-painful stimulus is presented to the test animal. Preferably, the means for presenting an aversive, non-painful stimulus to the test animal when the test animal is within the first chamber is a means for producing an aversive, non-painful condition (environment) within the first chamber. Preferably, the means for presenting an aversive, non-painful stimulus to the test animal when the test animal is within the second chamber is a means for producing an aversive, non-painful condition (environment) within the second chamber. The means for presenting an aversive, non-painful stimulus can be independently activated and deactivated. Each aversive, non-painful stimulus can be independently and rapidly presented and independently and rapidly removed. Therefore, by presenting a painful stimulus and/or an aversive, non-painful stimulus to the test animal, the test animal can be motivated to exhibit an escape response, such as exiting the chamber it is occupying and moving through the passageway into another chamber.

Preferably, each means for producing an aversive, non-painful condition is one or more light sources for lighting the interior of the respective chamber, thereby creating a lit environment. Preferably, each means for producing a painful condition is a means for independently heating and cooling the respective chamber floor.

Optionally, the apparatus can include a means for exhibiting an escape response (other than the test animal's movement between chambers). The escape response exhibiting means can be, for example, a lever, button, switch, or other actuating mechanism that, when activated by the test animal, terminates or lessens the magnitude of the aversive, non-painful stimulus or the painful stimulus. Thus, the test animal's activation of the escape response exhibiting means is the test animal's escape response (escape behavior). In addition, the apparatus can include a means for implementing an appetitive stimulus, which can likewise be activated by a lever, button, switch, or other actuating mechanism.

Optionally, the apparatus can include a tether system or wireless system to transmit signals to the test animal (e.g., electrical stimuli, chemical stimuli, pharmacological stimuli, optical signals, taste signals, olfactory signals, thermal signals). The signal sent to the test animal via tether or wireless link can be painful, aversive and non-painful, appetitive, addictive, or it can have a modulatory effect on the processing of stimuli delivered by other means (e.g., heating and cooling of the chamber floor). The signal sent to the test animal can be designed to generate anxiety, depression, or other emotional states, some of which are known to have a profound effect on pain processing. The trained test animal can choose when to initiate or terminate the stimulus (painful, aversive and non-painful, appetitive, addictive) by moving from one chamber into the other, or by activating the escape response exhibiting.

The apparatus can also include means for sensing the presence of the test animal within the first chamber and a means for sensing the presence of the test animal within the second chamber. The apparatus can be automated and used in conjunction with computer software for control of experiment conditions, response measurements, and data analysis.

The subject invention also concerns methods for using the subject apparatus to conduct escape latency tests, place preference tests, and control tests for each.

DETAILED DISCLOSURE OF THE INVENTION

Figure 1:
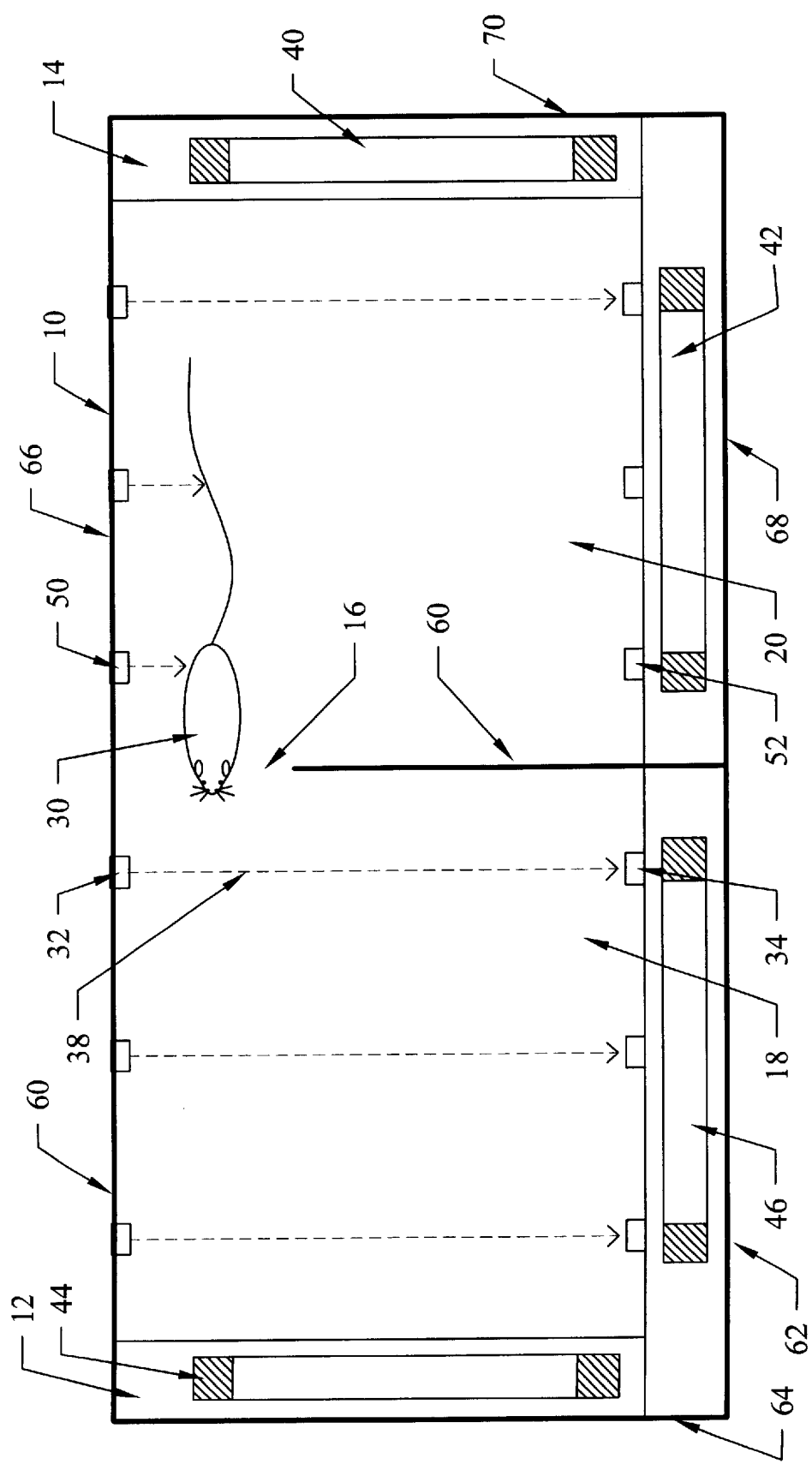
FIG. 1 shows an overhead view of one embodiment of the apparatus of the subject invention.

The present invention measures conscious learned escape behaviors as indicators of the pain experience that drives these behaviors. Using the subject invention as an animal model, an investigator can predict or extrapolate human clinical pain. The subject invention gives the investigator a choice of pain stimuli, which is advantageous in view of the fact that different modalities are processed differently by the neural systems. The pain stimulus can be, for example, thermal (contact heat or cold), electrical, or chemical (such as through a tether system). In addition, the subject invention is designed to discriminate between (pathological or interventional) effects on sensory vs. motor/behavioral aspect of pain: it offers a choice of non-nociceptive aversive stimuli (e.g., bright light, environmental climate, or chemical signals through tether) to trigger the same escape responses used in the pain test.

The subject invention concerns an apparatus 10 for testing the pain sensitivity exhibited by a test animal 30. The apparatus 10 can be used to evaluate the pain sensitivity of the test animal 30 in response to a disease state, drug, or other intervention, such as a surgical procedure. The apparatus 10 is designed to measure a conscious escape response to a painful stimulus in a test animal 30. The subject invention also pertains to methods for evaluating pain sensitivity exhibited by a test animal 30, in response to a drug, disease condition, or other intervention, using the subject apparatus 10.

The apparatus 10 includes one or more chambers within which the test animal 30 can be introduced. In a preferred embodiment, the apparatus 10 of the subject invention includes two chambers, a first chamber 12 and a second chamber 14, connected by a passageway 16. The passageway 16 is of sufficient size to permit the test animal 30 to pass between the chambers 12, 14. The apparatus 10 also includes means for presenting a painful stimulus to the test animal 30, when the test animal 30 is within said first chamber 12, and means for presenting a painful stimulus to the test animal 30 when the test animal 30 is within said second chamber 14. Preferably, the means for presenting a painful stimulus to the test animal 30 when the test animal 30 is within the first chamber 12 is a means for producing a painful condition within the first chamber 12. Preferably, the means for presenting a painful stimulus to the test animal 30 when the test animal 30 is within the second chamber 14 produces a painful condition within the second chamber 14. Each painful stimulus can be independently and rapidly presented when the test animal 30 is within the respective chamber and independently and rapidly removed. In the case where the means for presenting painful stimulus is a means for producing a painful condition within a chamber, the painful condition can be independently and rapidly produced and independently and rapidly removed.

The apparatus 10 further includes means for presenting an aversive, non-painful stimulus when the test animal 30 is within each of the chambers 12, 14. Preferably, the means for presenting an aversive, non-painful stimulus to the test animal 30 when the test animal 30 is within the first chamber 12 is a means for producing an aversive, non-painful condition within the first chamber 12. Preferably, the means for presenting an aversive, non-painful stimulus to the test animal 30 when the test animal 30 is within the second chamber 14 is a means for producing an aversive, non-painful condition within the second chamber 14. Each aversive, non-painful stimulus can be independently and rapidly presented and independently and rapidly removed. In the case where the means for producing the aversive, non-painful stimulus produces an aversive, non-painful stimulus within a chamber, the condition can be independently and produced and independently and rapidly removed.

The apparatus 10 can also include means for sensing the location of the test animal 30 within the apparatus 10 (e.g., which chamber the test animal 30 is in). Each means for presenting an aversive, non-painful stimulus to the test animal 30 present a stimulus that is aversive to the test animal 30 within each chamber 12, 14 where the means for presenting an aversive, non-painful stimulus are activated. Preferably, each means for presenting a painful stimulus and each means for presenting an aversive, non-painful stimulus is adjustable in its intensity.

As used herein, the term "rapidly produced" means that an aversive stimulus is rapidly presented to the test animal 30. Where the aversive stimulus is presented as an aversive environment or condition within a chamber, the condition is preferably rapidly created within the particular chamber 12, 14 that the means for producing the painful condition and/or the means for producing the aversive, non-painful condition are activated. The term "rapidly removed" means that aversive stimulus is rapidly removed from presentation to the test animal 30. Where the aversive stimulus is presented as an aversive environment or condition within a chamber, the condition is rapidly removed from within the particular chamber 12, 14 that the means for producing the painful condition and/or the means for producing the aversive, non-painful condition are de-activated. Preferably, a painful stimulus and an aversive, non-painful stimulus can each be presented to the test animal 30 in about 30 seconds or less, and a painful stimulus and an aversive, non-painful stimulus can each be removed in about 30 seconds or less. More preferably, a painful stimulus and an aversive, non-painful stimulus can each be presented to the test animal 30 in about 10 seconds or less, and a painful stimulus and an aversive, non-painful stimulus can each be removed in about 10 seconds or less. Most preferably, a painful stimulus and an aversive, non-painful stimulus can each be presented to the test animal 30 in about 5 seconds or less, and a painful stimulus and an aversive, non-painful stimulus can each be removed in about 5 seconds or less.

Each chamber 12, 14 has a surface for supporting the test animal 30 (e.g., a floor). Each floor 18, 20 can be a continuous surface or a perforated surface (e.g., a wire mesh). The chamber floors 18, 20 should be of sufficient surface area to enable the particular type of test animal 30 being used to move about the apparatus 10. For example, where the test animal 30 is a rat, the first and second chambers 12, 14 can each be about 22 cm×22 cm×24 cm.

Preferably, the means for producing a painful condition in the first chamber 12 is a means for independently heating and cooling 22 the first chamber floor 18, and the means for producing a painful condition in the second chamber 14 is a means for independently heating and cooling the second chamber floor 20, such that thermal pain stimulation (e.g., aversive heat or aversive cold) can be provided to the paws of the test animal 30 while they contact either of the chamber floors 18, 20. When the means for producing the painful condition are means for independently heating and cooling the chamber floors 18, 20, each of the chamber floors 18, 20 are preferably composed of a thermally conductive material that is corrosive resistant, such as copper or aluminum. More preferably, the chamber floors 18, 20 are composed of copper.

More preferably, one or more thermoelectric modules ("TEMs"; also known as Peltier devices) 24 located beneath each of the chamber floors 12, 14, can be used as heat pumps to move heat to and from the chamber floors 12, 14. A TEM 24 contains a number of p-type and n-type pairs (couples) connected electrically in series and sandwiched between two ceramic plates. When connected to a DC power source, current causes heat to move from one side of each TEM 24 to the other side, creating a hot side and a cold side. If the current is reversed (reversing the polarity of the power supply), the heat is moved in the opposite direction, with the hot face becoming the cold face and vice-versa. TEMs 24 are particularly well suited for use in the apparatus 10 of the subject invention because they are solid-state devices that can provide precision temperatures, with no moving parts. Therefore, they produce virtually no noise to distract the test animal 30, which could potentially skew experimental results. The amount of heat pumped through the TEM 24 is directly proportional to the power supplied. Temperature can be controlled through manual or automatic means. The automatic temperature controller utilized can range in complexity from a simple on-off thermostat to a complex computer controlled feedback proportional control loop.

The TEMs 24 are located beneath, and preferably in contact with, the chamber floors 18, 20. More preferably, the TEMs 24 are located between the chamber floors 18, 20 and a heat sink 26. There are at least two heat sinks, one heat sink 26 beneath, and in contact with, each chamber floor. Each heat sink 26 is preferably a liquid-type heat sink composed of aluminum and containing channels 28 to remove heat from the surface of the TEM 24 that contacts it, or to supply heat to the surface of the TEM 24 that contacts it, depending upon the direction the heat is pumped by the TEM 24. Other types of heat sinks, such as fin-type heat sinks, with or without fans, can also be utilized.

In order to maximize heat transfer between each TEM 24 and each heat sink 26, and between each TEM 24 and the corresponding chamber floor, a film of heat conducting medium, such as zinc oxide paste, can be applied to the top and bottom surface of the TEM 24.

By using one or more TEMs 24 as the heating and cooling means 22 beneath each chamber floor 18, 20, it is possible to modulate the temperature of the chamber floors 18, 20 very rapidly from an aversive temperature to a neutral, steady-state temperature (e.g., 39° C.), and vice-versa, and ranges there between. For example, it is possible to modulate the temperature of the chamber floors 18, 20 about 10° C. in about ten seconds or less, and even five seconds or less, within a temperature range of about 0° C. to about 60° C.

When using means for independently heating and cooling the chamber floor, aversive cold temperatures can be from about 0° C. to about 10° C. for cold stimulus or about 43° C. to about 49° C. for heat stimulus. Preferably, temperatures from about 0° C. to about 1° C. are used for cold stimulus, temperatures from about 43° C. to about 45° C. are used for heat stimulus to test slow conducting nerve fiber systems, and temperatures from about 47° C. to about 49° C. are used for heat stimulus to test fast conducting nerve fiber systems.

Another means for producing a painful condition within each chamber, that can be independently and rapidly produced and removed, involves placement of one heat sink 26 beneath, and in contact with, each chamber floor. However, instead of utilizing one or more TEMs 24 beneath each chamber floor, each heat sink 26 is connected with a source of hot liquid and a source of cold liquid, with flow between the heat sink 26 and the sources of hot and cold liquid controlled by one or more valves. The hot and cold liquid can be rapidly pumped into and out of the heat sink 26, as required, by one or more liquid pumps. In another embodiment, instead of being located beneath the chamber floor, each heat sink 26 can itself serve as the chamber floor.

Both means for presenting a painful stimulus can be a single "unit" that can be manipulated (manually or automatically) to administer a pain stimulus to the test animal within either chamber, such as an array of TEMs that are moved from beneath one chamber floor to another chamber floor, as required. Preferably, the means for presenting the painful stimulus represents two separate units, such as an array of TEMs located beneath each chamber floor. Although separate, each unit can be in operable communication.

Ambient air temperature can be utilized to produce a painful condition, an aversive non-painful condition, or an appetitive condition for the test animal. For example, the means for producing a painful condition can be one or more radiators that circulate the air in a given chamber to produce a controlled air-conditioned environment with temperatures (hot or cold) that are painful to the test animal. The test animal's response to the climatic stimulus can be measured as escape latency or place preference. In one embodiment, climatic stimuli and other stimuli (e.g., thermal floor stimuli, light stimuli, stimuli through tether or wireless link) can be titrated against each other. This embodiment of the apparatus is useful in assessing the responsiveness of the autonomic nervous system, which is critical for thermoregulation of the body. The autonomic system plays a significant role in certain pain conditions. Treatments such as drugs can be tested for their effect on autonomic function. The sensory quality or unpleasantness of a climate is inferred from the test animal's movement between chambers, or from preference of a chamber. In conjunction with the climatic stimuli, the tether or wireless transmission system can be used to sample physiological variables related to autonomic function, or to modulate the autonomic nervous system.

The passageway 16 is of sufficient size for the test animal 30 to pass freely between the chambers 12, 14. For example, where the test animal 30 is a rat, the passageway 16 can be about 6.5 centimeters wide. Preferably, the passageway 16 has no overhead door jam, thereby permitting unfettered passage of the test animal 30 if the animal is tethered, e.g., with electrical leads, microdialysis tubes, or other diagnostic or drug delivery devices. It is also preferred that the passageway 16 be sufficiently short (such as a portal), such that the test animal 30 will always be in contact with at least one of the chamber floors, thereby requiring the test animal 30 to pass from one chamber directly to another.

The apparatus 10 of the invention shown in FIG. 1 includes means for producing an aversive, non-painful condition within the first chamber 12 and means for producing an aversive, non-painful condition within the second chamber 14. Each means for producing an aversive, non-painful condition creates an aversive condition within the particular chamber that the means for producing the aversive, non-painful condition is activated.

Preferably, each means for producing an aversive, non-painful condition is one or more light sources for lighting the interior of the chambers 18, 20, such as a fluorescent light. If each means for producing an aversive, non-painful condition is one or more light sources, it is preferred that the passageway 16 be large enough to allow the test animal 30 to pass freely but sufficiently small to minimize the amount of light that enters each chamber 12, 14 when one chamber is dark and the other chamber is lit. In a specific embodiment, the first chamber 12 has two light sources 40 and 42, and the second chamber 14 has two light sources 44, 46, as shown in FIG. 1.

Another example of light sources that can be utilized as means for producing an aversive, non-painful condition are light emitting diodes (LEDs). LEDs are particularly useful because they generate less heat and their light emission does not deteriorate over time.

Other means for producing an aversive, non-painful condition, which can be independently and rapidly produced and removed, include means for producing a sound that is aversive to the test animal 30 (e.g., an electronic audio player), or means for producing a smell that is aversive to the test animal 30, for example. The aversive smell can be rapidly produced and removed by a fan or other circulation means.

The means for presenting the aversive, non-painful stimulus can be a single "unit", such as a moveable light source that can be manipulated (manually or automatically) to direct aversive light into each chamber, thereby producing an aversive, non-painful condition, or the means for presenting the aversive, non-painful stimulus can be two separate units, such as separate light sources mounted within, or adjacent to, each chamber. Although separate, each unit can be in operable communication.

The location of the test animal 30 within the apparatus at a given time can be determined visually by an operator either directly or indirectly, e.g., directly via eyesight or with a video camera. However, the apparatus 10 of the subject invention can also include means for sensing the presence of the test animal 30 within each chamber 12, 14. Preferably, there is a means for sensing the presence of the test animal within the first chamber 12 and a means for sensing the presence of the test animal within the second chamber 14. More preferably, means for sensing the presence of the test animal in the first chamber includes one or more infrared beam emitters 32 and detectors 34 within the first chamber 12, where the beam emitters 32 and detectors 34 are operably positioned, producing one or more infrared beams 38 in the first chamber 12. Means for sensing the presence of the test animal in the second chamber 14 includes one or more infrared beam emitters 50 and detectors 52 in the second chamber 14, where the emitters 50, and detectors 52 are operably positioned, producing one or more infrared beams 38 in the second chamber 14. As used herein, the term "operably positioned" means that the emitters 32, 50 and detectors 34, 52 are at a predetermined position with respect to each other such that one or more infrared beams 38 are emitted and detected in each chamber, and interruption of the infrared beams 38 by the test animal 30 produces a signal indicating the location of the test animal 30 within the test apparatus 10 (e.g., indicating which chamber 12, 14 the test animal 30 is in). The apparatus 10 can also include means for measuring the relative amount of time the test animal 30 is present in each chamber 12, 14 and, optionally, determining the number of entries in each chamber 12, 14.

In a separate embodiment, the apparatus 10 can include one or more infrared beam emitters and detectors within the passageway 16. Interruption of one or more infrared beams 38 produces a signal indicating that the test animal 30 has passed through the passageway 16. If the original position of the test animal 30 is known, the position of the test animal 30 within the apparatus (i.e., within which chamber) at a given time can be surmised based on the number of times the test animal 30 has passed back and forth through the passageway 16.

Other means for sensing the location of the test animal 30 within the apparatus 10 include ultrasound localization, digital image analysis, or monitoring electrical capacitance of the chamber floors 18, 20, for example.

In a preferred embodiment, the shape and dimensions of the chambers 12, 14 are substantially identical to one another. For purposes of the subject invention, in this context, the term "substantially identical" means that the particular test animal 30 used cannot discriminate between the two chambers 12, 14, based upon their shape and dimensions. It is preferred that the chambers 12, 14 be designed to provide non-painful distinct visual and tactile environments to minimize contextual differences.

Optionally, wireless telemetry can be utilized to obtain diagnostic information (e.g., biological information) concerning the test animal. Wireless telemetry systems include, for example, radio-electric transmission, optical transmission, ultrasound transmission, or other transmission technologies that do not rely on a continuous wire, lead, or cable connection between the test animal and any external equipment. Wireless systems include a means for transmitting the information, which is connected to or contained within the test animal 30, and a means for receiving the transmitted information, which is separated from the transmitting means and, optionally, placed at a location remote from the chambers.

Optionally, the apparatus can include a means for exhibiting an escape response (other than the test animal's movement between chambers). The escape response exhibiting means can be, for example, a lever, button, switch, or other actuating mechanism that, when activated by the test animal, terminates or lessens the magnitude of the aversive non-painful stimulus or painful stimulus. When the escape response exhibiting means is activated by the test animal, the aversive non-painful stimulus or painful stimulus can be automatically terminated or lessened in magnitude, or activation of the escape response exhibiting means can signal an experimenter/operator to terminate or lessen the magnitude of the aversive non-painful or painful stimulus. As indicated above, the apparatus 10 is designed to measure a conscious escape response to a painful stimulus in a test animal 30. The conscious escape response to the painful stimulus exhibited by the animal can be the test animal's movement from one chamber to another or the animal's activation of the escape response exhibiting means.

The apparatus can include a means for implementing an appetitive stimulus to the test animal. The appetitive stimulus implementing means can be a mechanism similar to the escape response exhibiting means that can operate similarly to provide an appetitive stimulus to the test animal when activated by the test animal. Contingencies (responses that "turns on" or "turns off" a stimulus) can be defined for enabling or disabling the escape response exhibiting means and the appetitive stimulus implementing means. Chambers containing levers that use the timing and frequency of lever-press action as the measured response are well known (see Skinner and Campbell, *Journal of Comparative and Physiological Psychology*, 1947, 40:305–307). The conscious escape response exhibiting means and the appetitive stimulus implementing means can be located anywhere within a chamber, such as disposed or fixed to a floor or wall, suspended from a ceiling/cover, etc.

Optionally, the apparatus can include a tether system or wireless system to transmit or otherwise deliver signals to the test animal (e.g., electrical stimuli, chemical stimuli, pharmacological stimuli, optical signals, taste signals, olfactory signals, thermal signals). Therefore, the means for presenting a painful stimulus to the test animal and the means for presenting an aversive non-painful stimulus to the test animal can include a tether system or wireless system that deliver the painful stimulus or aversive non-painful stimulus to the animal via a signal. For example, tethered or remote controlled indwelling catheter can be used to deliver a pharmacological agent to the test animal. For example, optical signals can be transmitted directly into optically sensitive physiological structures within the test animal, taste signals transmitted directly can be transmitted directly to the oral cavity of the test animal, olfactory or pheromone signals can be transmitted directly to the nasal cavity of the test animal, or thermal signals can be generated by devices implanted or attached to the animal and controlled through the tether or wireless link.

The signal sent to the test animal via tether or wireless link can be painful, aversive but non-painful, appetitive, addictive, or the signal can have a modulatory effect on the processing of stimuli delivered by other means (e.g., heating and cooling of the chamber floor). The signal sent to the test animal can be designed to generate anxiety, depression, or other emotional states, some of which are known to have a profound effect on pain processing. The trained test animal can choose when to initiate or terminate the stimulus (painful, aversive and non-painful, appetitive, addictive) by moving from one chamber into the other, or by activating the escape response exhibiting means. The same tether system or wireless system, or different systems, can be utilized to deliver different types of stimuli simultaneously or at different times, such as painful stimulus and appetitive stimulus. Therefore, the tether system or wireless system can be utilized to deliver painful stimulus, aversive non-painful stimulus, appetitive stimulus, addictive stimulus, or combinations thereof.

The test animal 30 can be any animal having nociceptors (receptors for pain stimuli) and which is capable of exhibiting an escape response to a pain stimulus. According to the apparatus and methods of the subject invention, the escape response can be a behavior such as exiting one chamber to enter another chamber or activating a means for exhibiting an escape response, such as a lever, button, switch, or other actuating mechanism. Preferred animals are those having a physiology sufficiently similar to humans such that they provide relevant correlative data, as an animal model, for the particular treatment being conducted on the animal. Examples of appropriate animals include those of the order rodentia, such as members of the family muridae (e.g., mice, rats, hamsters, voles, lemmings, and gerbils), lagomorpha (e.g., rabbits, pikas, and hares), and caviidae (e.g., guinea pigs), or those of the order insectivora, such as members of the family soricidae (shrews) and talpidae (moles), and so forth. In addition, if a light source is used as the means for producing the aversive, non-painful condition, it is preferred that the test animal be one that has an aversion to brightly lit areas, such as rodents (Ogren, S. O., *Acta Physiol Scand Suppl,* [1985], 544:1–71).

The apparatus 10 of the subject invention can be partially or fully automated. Therefore, the apparatus can also include means for automating the means for presenting a painful stimulus and the means for presenting an aversive, non-painful stimulus in response to the sensing means in both chambers. The automation means can be in operable communication with the features being automated. For example, when the test animal 30 passes through the passageway 16 from the first chamber 12 to the second chamber 14, the means for producing an aversive, non-painful condition can be automatically activated or deactivated in the second chamber 14, and when the test animal 30 passes through the passageway 16 from the second chamber 14 to the first chamber 12, the means for producing an aversive, non-painful condition can be automatically activated or deactivated in the first chamber 12. The same automation can be achieved with the means for producing a painful condition when the test animal 30 is in the first chamber 12 and the means for producing a painful condition when the test animal 30 is in the second chamber 14.

Because the apparatus 10 of the subject invention can be used to conduct an escape test and a well-matched, paired motor control test, inclusively, within the same apparatus, and because the painful condition and the aversive, non-painful condition can be rapidly produced and removed within each chamber, the apparatus 10 of the subject invention can be used to evaluate the pain sensitivity of a test animal within the same day and even within the same hour. This is important because the physiological and behavioral status of many test animals can vary within a month or even within a day, affecting experimental results.

In one embodiment, the thermal (heat or cold) stimulus from the chamber floor and/or bright light stimulus can be used in combination with stimuli transmitted through the tether or through wireless transmission. This embodiment of the apparatus of the subject invention can be utilized for testing the addictiveness of a substance, such as a drug. For example, the test animal 30 receives an appetitive stimulus (e.g., such as by microinfusion of a compound through a tether) only when it resides in the brightly lit chamber. The test animal's willingness to tolerate the unpleasantness of bright light in exchange for experiencing the pleasant sensation generated by the substance can serve as a predictor of the appetitive or addictive properties of the substance.

The means for automation can include one or more computer programs that can control the activation, deactivation, and intensity of the means for presenting the painful stimulus (e.g., set the floor temperatures) and the means for presenting the aversive, non-painful stimulus (e.g., light sources), as well as sense and record the movements of the test animal 30 within the apparatus 10, e.g., between within a single chamber or between two or more chambers. For example, the pain sensitivity test can be conducted on a test animal and the results can be compared with that of the test of general motivation and motor ability as a control. Both tests and the comparison of results can be conducted through automation. The means for automating one or more of: (i) the means for presenting a painful stimulus when the test animal is in the first and second chambers, (ii) the means for presenting an aversive, non-painful stimulus when the test animal is in the first and second chambers, and (iii) the means for sensing the presence of the test animal within the first and second chambers can be in operable communication with an interface device to receive commands from an operator of the device. The interface device can display menus for directing the automation means, e.g., specifying various experiment parameters and conditions within the first and second chambers.

The chamber walls can be constructed of a variety of materials, such as plastic, wood, metal, or glass. The chamber walls can be completely or partially transparent, or opaque. Preferably, the chamber walls are transparent (e.g., constructed of PLEXIGLAS), permitting easy observation of the test animal within the apparatus 10. In this case, it is also preferable to create a one-way mirror effect by tinting the walls of the chambers and dimming the light in the outside environment to minimize distractions for the test animal. The chambers can be a variety of shapes (e.g., square, triangular, circular, etc.), with the number of walls depending upon the shape.

Preferably, the chambers 12, 14 have lids or are otherwise covered to minimize outside stimuli, e.g., from the laboratory environment.

In a specific embodiment, the first and second chambers 12, 14 are adjacent to one another, each chamber having three walls and a fourth 60, which is shared between the two chambers 12, 14. In this embodiment, the fourth wall 60 roughly bisects the apparatus 10, but incompletely separates the two chambers 12, 14, and defines the passageway 16 that connects the chambers 12, 14, as shown in FIG. 1. Preferably, the chambers of the apparatus of the present invention are not concentric such that one chamber is contained within another, but rather are connected adjacent to one another.

The apparatus of the subject invention preferably includes two chambers, but may include more chambers and more passageways connecting the chambers, as required by the specific experiment protocols. Preferably, the apparatus is modular in design in that additional chambers can be added to connect with other chambers. Optionally, passageways between chambers can be closed by barriers that keep the test animal 30 from passing through a given chamber. In this way, different chambers in a multiple chamber system can be utilized by making only some chambers available to the test animal 30.

If one or more light sources that radiate excessive amounts of heat are used as the means for producing a painful condition in either chamber, it is preferable to block the heat with a heat-absorbing filter. If means for independently heating and cooling the floors of each chamber 12, 14 are used as the means for producing a painful condition, an excessive rise of the ambient temperature within the chambers 12, 14 can be prevented by forced air circulation, as with a fan in one or more chambers.

Preferably, the test animal 30 is not restrained in the apparatus 10, thereby eliminating the confounding factor of restraint stress, which is known to affect pain sensitivity.

A treatment being tested with the apparatus 10 of the subject invention can include administration of a substance (e.g., a drug or nutraceutical), a surgical procedure, or other intervention that is being evaluated for its effects on pain sensitivity or general effects on operant behavior. A treatment being tested can be either hyper-analgesic (decreasing normal pain sensitivity) or hypo-analgesic (increasing pain sensitivity beyond that which is normal). Furthermore, the treatment can be genetic manipulation conducted on either the test animal itself, or one or more of the test animal's forebears. For example, "knock out" animals can be tested with the apparatus of the subject invention to study the effects of the knocked out gene or genes on nociception with or without further treatment. The test animal 30 can be suffering from a disease state or other pathological condition. The pain sensitivity of the test animal 30 suffering from a disease state or pathological condition can be evaluated with the subject apparatus 10, with or without treatment. Therefore, the apparatus of the subject invention can be used to test the general pain sensitivity exhibited by a test animal 30, in whatever condition the test animal 30 is in, naturally occurring or artificially induced.

Advantageously, the apparatus of the subject invention can allow simultaneous sampling of behavioral and multiple physiological variables in conscious unrestrained animals over a prolonged period of time. This feature is becoming progressively more important as the scientific community begins to appreciate that sensory experience is a result of many external and internal physiological signals interacting in a network fashion. Using the apparatus of the subject invention, an experimenter can isolate one variable while keeping the other variables constant, or an experimenter can manipulate multiple variables simultaneously to study their interaction.

As used herein, the terms "operable communication" and "operably connected" mean that the particular elements are connected in such a way that they cooperate to achieve their intended function or functions. The "connection" is a link that may be direct or indirect, physical or remote.

As used herein, references to "first," "second," and the like (e.g., first and second chambers, first and second light sources) are intended to identify a particular feature of which there are at least two. However, these references are not intended to confer any order in time, structural orientation, or sidedness (e.g., left or right) with respect to the particular feature.

As used herein, it should be understood that the terms "painful stimulus" and "painful condition" are relative terms, meaning that the stimulus or condition will be potentially painful, but the actual pain perceived by the test animal 30 will ultimately depend upon the pain sensitivity of the test animal 30. The definition of clinical pain, as used herein, is described in the background section of the application. A painful condition is intended to refer to an environment that is created in a given chamber and which is potentially painful to the test animal 30 when the test animal 30 is within the chamber. Examples of painful conditions include heated or cooled floors, or heated or cooled air. A painful stimulus is intended to be inclusive of a painful condition. Examples of painful stimuli include heated or cooled floors, heated or cooled air, as well as painful stimuli presented directly to the test animal 30, such as through a tether system or wireless system.

As used herein, the term "appetitive stimulus" is intended to mean a stimulus that is pleasant or wanted by the test animal. The appetitive stimulus can be, for example, a pleasurable sensation caused by delivery of a chemical, electrical, or pharmacological stimuli via a tether system or wireless system, or the appetitive stimulus can be cessation or lessening of an aversive stimulus (whether painful or non-painful). An appetitive stimulus generally increases a behavior it follows.

As used herein, the term "aversive stimulus" is stimulus that the test animal will usually avoid or seek to escape from. An aversive stimulus generally suppresses behavior it follows and increases behavior which allows a test animal to escape and avoid it.

As used herein, the term "escape response" or "escape behavior" reduces or removes aversive stimulation (whether painful or non-painful). The escape response can be, for example, movement of the test animal from one chamber to another or activation of a conscious escape response exhibiting means).

The terms "comprising", "consisting of", and "consisting essentially of" are defined according to their standard meaning and may be substituted for one another throughout the instant application in order to attach the specific meaning associated with each term.

All patents and publications referred to or cited herein are incorporated by reference in their entirety to the extent they are not inconsistent with the explicit teachings of this specification.

Following are examples which illustrate procedures for practicing the invention. The examples should not be construed as limiting.

EXAMPLE 1

Operant Test Apparatus Utilizing Light and Thermoelectric Modules

The first and second chambers 12, 14 are adjacent to one another, each chamber having three walls and a fourth 60, which is shared between the two chambers 12, 14. The fourth wall 60 roughly bisects the apparatus 10, but incompletely separates the two chambers 12, 14, and defines the passageway 16 that connects the chambers 12, 14, as shown in FIG. 1. The first chamber 12 has two side walls 60, 62 and one end wall 64. The second chamber 14 has two side walls 66, 68, and one end wall 70. The first chamber 12 has two light sources 40 and 42, one within the side wall 62 most distant from the passageway 16 and the other in the end wall 64. The second chamber 14 has two light sources 44, 46, one within the side wall 68 most distant from the passageway 16, and one within the end wall 70, as shown in FIG. 1. The chamber walls containing light sources are sufficiently transparent to allow passage of light into the respective chambers at aversive levels.

Figure 2A:
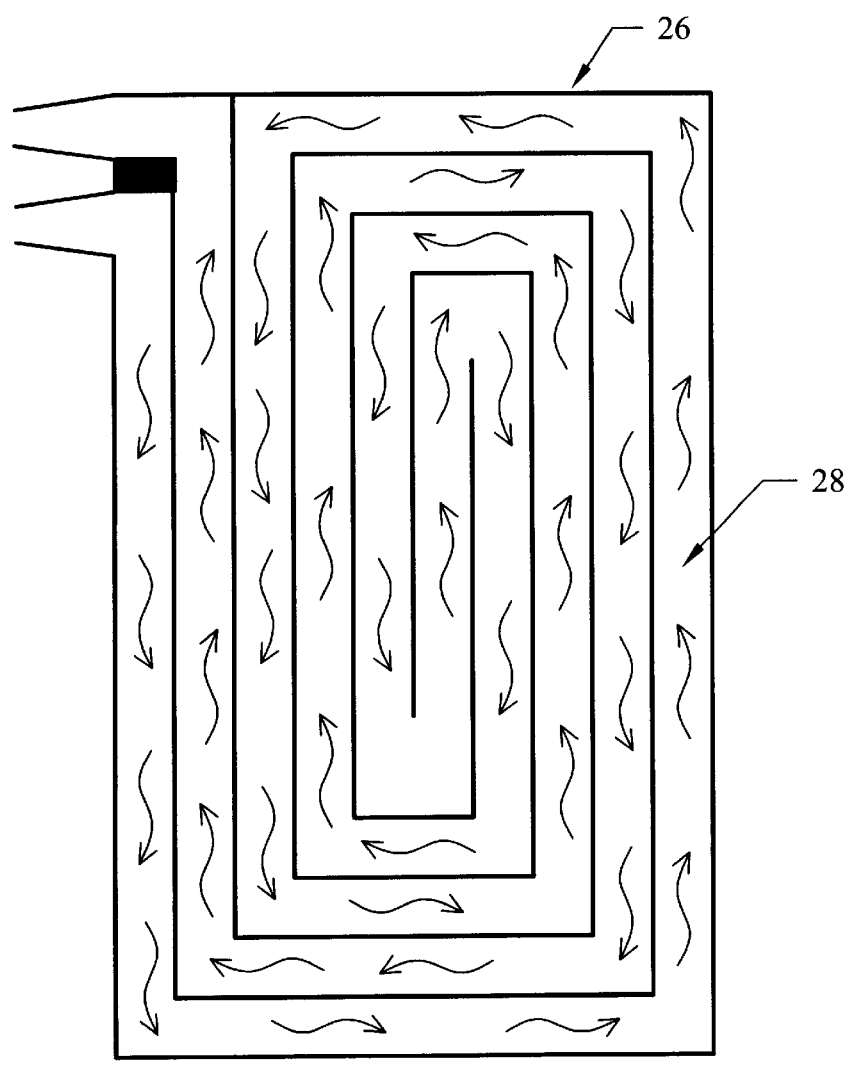
FIG. 2A shows a transparent overhead view of the floor of a chamber in one embodiment of the subject invention. Channels for flow of heated or cooled fluid through the heat sink are shown.
Figure 2B:
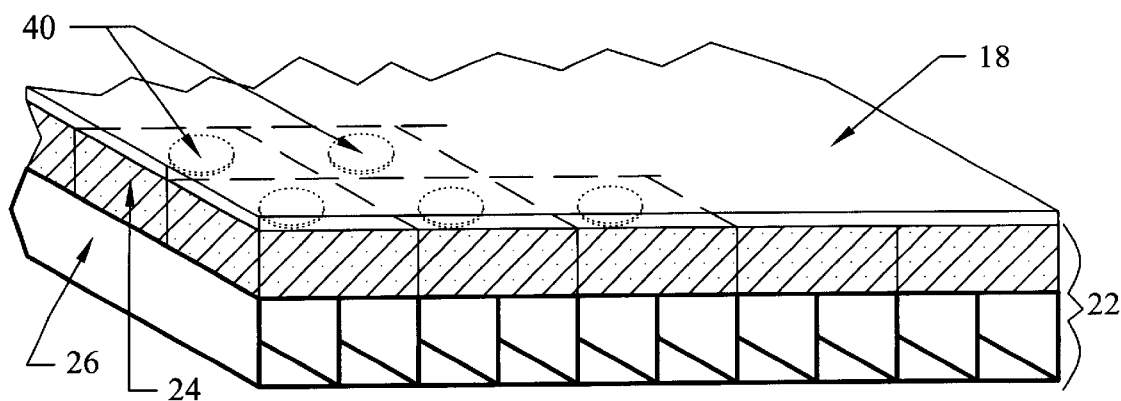
FIG. 2B shows a side view of the floor of a chamber in one embodiment of the subject invention. The floor, thermistors, thermoelectric modules, and heat sink are shown.

The chamber floors 12, 14 are composed of copper and the means for heating and cooling 22 the floors are one or more thermoelectric modules (TEMs) 24 and a heat sink 26, with the TEMs between the chamber floors and the heat sink, as shown in FIG. 2B. The heat sink 26 is a fluid-type heat sink composed of aluminum and containing channels 28 for fluid circulation adjacent to the TEMs 24, as shown in FIG. 2A. Fluid can be continuously pumped through the heat sink 26 at 15 liters/minute, serving as a thermal carrier. Preferably, the fluid is a mixture of ethylene glycol (about 20%) and distilled water (about 80%). The temperature of the chamber floors 18, 20 can be adjusted from freezing temperatures, through the tolerable range of heat, to painfully hot temperatures, as required by the specific experimental situation.

TEMs 24, also known as Peltier devices, are commercially available (MELCOR, Trenton, N.J.) and used to move heat (i.e., a heat pump). When current from a power source passes through the junction of two different types of conductors, it results in a temperature change. The current causes heat to move from one side of the TEM to the other, creating a hot side and a cold side on the TEM. At the cold junction, energy (heat) is absorbed by electrons as they pass from a low energy level in the p-type semiconductor element, to a higher energy level in the n-type semiconductor element. The power supply provides the energy to move the electrons through the system. At the hot junction, energy is expelled to a heat sink as electrons move from a high energy level element (n-type) to a lower energy level element (p-type).

Thermoelectric cooling "couples" can be made from two elements of semiconductor, such as bismuth telluride, doped to create either an excess (n-type) or deficiency (p-type) of electrons. Heat absorbed at the cold junction is pumped to the hot junction at a rate proportional to current passing through the circuit and the number of couples. Thermoelectric cooling couples are combined and arrayed in a module, where they are connected electrically in series and thermally in parallel (i.e., pumping together in the same direction). Modules are available in a variety of sizes, shapes, operating currents, operating voltages, and ranges of heat pumping capacity.

A plurality of TEMs 24 can be used side-by-side to increase the amount of heat pumped, as shown in FIG. 2B, or they can be stacked on top of one another (i.e., "cascades" or "multistage TEMs") to increase the temperature difference across the TEM 24. Typically, when the temperature difference doesn't need to be more than about 60° C. to about 67° C., single-stage TEMs are sufficient. If the temperature difference needs to be greater than about 60° C. to about 67° C., cascades should be considered. The amount of heat pumped through the TEM 24 is directly proportional to the power supplied.

Preferably, the channels 28 of the heat sink 26 are arranged such that the temperature is uniform (e.g., within about ±0.1° C.) across the entire surface of the heat sink. The fluid circulation is closed and the system includes a 7-liter bath containing the water/ethylene glycol medium and a pump of about 15 liters/minute capacity. A temperature controller, such as a DPDT relay, which is wired in the classic polarity-reversal configuration, can be used to switch between heating and cooling modes. One or more thermistor probes 40 (thermally sensitive resistor), shown in phantom in FIG. 2B, can be used to sense the temperature of each of the chamber floors. The thermistor probes 40 can be located between each TEM 24 and the chamber floor. In order to maintain close contact between the chamber floors 12, 14 and the TEMs 24, the underside of the chamber floors 12, 14 can have recesses for containing the thermistor probes 40. In FIG. 2B, the phantom lines surrounding the thermistor probes 40 represent the individual TEMs 24 beneath the chamber floor.

The temperature controller, which is in operable communication with the thermistor probe 40 and each TEM 24, can be used to set the temperature and provide the DC current that drives the TEMs 24. The use of electronically regulated TEMs 40 compensates for thermal disturbances such as paw contact or urine released by the test animal 30. Furthermore, this design allows temperatures of the chamber floors 18, 20 to be changed within seconds, e.g., to reverse the temperature between chambers 12, 14, in order to prevent the test animal 30 from associating one of the chambers with a certain experimental condition.

EXAMPLE 2

Experimental Methods and Pain Tests

The following experiments are described where the test animal 30 is a rat, each means for presenting an aversive, non-painful stimulus is a means for producing an aversive, non-painful condition (in this case, it is a light source), and each means for presenting a painful stimulus is a means for producing a painful condition within a chamber (in this case, it is a means for independently heating and cooling the floors of each chamber 22); however, it should be understood that other embodiments may be used with different test animals and/or different stimuli. In most experiments, one chamber is kept thermally neutral and brightly lit. When introduced into the apparatus, the rat will move back and forth between chambers, but spend more time in the less aversive chamber. During each trial, the rat's place preference (relative amount of time spent in either chamber) can be determined and recorded. The direction of the aversiveness gradient (which chamber is hot and which chamber is light) can be randomly chosen, and changed periodically throughout the experiment, so the rat cannot learn to associate the aversive stimulus (hot floor) with any particular chamber. In other words, because the two chambers are, preferably, identical and the gradient of the two aversive forces (e.g., thermal and light) can be reversed within seconds, avoidance learning is prevented.

The capability of each aversive, non-painful condition and each painful condition to be independently and rapidly produced and independently and rapidly removed within each chamber (also referred to herein as "the reversible feature") prevents the test animal 30 from recognizing one of the chambers 12, 14 as potentially aversive. If the animal were to recognize a chamber as potentially aversive, it would lead to behavior based upon past experience (avoidance), rather than behavior triggered by pain perceived at the moment (escape). Therefore, the apparatus 10 and method of the subject invention measure a conscious escape response, which requires a higher level of neural processing than simple reflex behaviors. Conventional pain tests typically infer pain from spinal reflex responses, such as paw withdrawal and tail flick. Reflex tests are not well suited for measuring delayed pain from a low intensity thermal stimulus, but the delayed pain from such stimuli is a better model of persistent clinical pain than the sharp pain that is best for triggering reflexes. Therefore, the apparatus 10 permits evaluation of the effects of disease states, drugs, surgical procedures, or other interventions. on the delayed pain mediated by unmyelinated pain fibers, which is a better model of persistent clinical pain than tests measuring the early sharp pain that results from high stimulus intensities.

The apparatus 10 of the subject invention can be used to perform a variety of tests. An escape test can be conducted where the means for producing a painful condition is not activated in either chamber 12, 14 and the test animal 30 is introduced into the apparatus 10. An adaptation period may be granted. If means for independently heating and cooling the chamber floors is utilized as means for producing a painful condition, the test animal's paws can assume the neutral temperature of the chamber floors 12, 14 during this period. The first trial is started by activating the means for producing a painful condition in the occupied chamber, to the desired intensity of the test. If the test animal 30 perceives that particular intensity of the painful condition as aversive, the test animal 30 will escape into the other chamber. The delay in the escape into the other chamber serves as the response variable or response time (escape latency). This delay for the initial crossover event can be measured (e.g., by an observer or automatically, through means of sensing the presence of the test animal 30 within each chamber). After each trial, a timeout period can be granted where the means for producing a painful condition is not activated in either chamber. A new trial is initiated by activating the means for producing a painful condition in the chamber occupied by the test animal. The escape latency can then be measured again.

In order to determine the contribution of changes in general motivational state and motor factors to the observed latency changes, the escape test can be repeated, as a control test, where the means for producing an aversive, non-painful condition (e.g., bright light) are used, without either means for producing a painful condition being used. The escape latency from the chamber in which the aversive, non-painful condition is activated serves as the response variable for the control test (e.g., control escape latency).

A number of avoidance-suppressing features can be implemented, as well. In a typical protocol, the means for producing a painful condition is not always activated in the same chamber. Therefore, the test animal 30 cannot use location cues as predictors of a painful experience. Sporadically, trials can be conducted with the means for producing a painful condition deactivated in both chambers (e.g., both chambers are set to a neutral temperature). Consistent short-latency responses during these trials are indicative of avoidance learning. Frequent exposure to this type of catch trial helps to minimize the test animal's avoidance tendency (extinction effect). High incidence of avoidance during catch trials serves as a warning indicator of avoidance tendencies and thus the validity of results should be questioned. Additionally, trials can be conducted with the means for producing a painful condition activated in both chambers 12, 14, with the means for producing a painful condition set at a higher intensity in the chamber that the test animal 30 is escaping to (the escape chamber), than that chamber it is escaping from. An avoidance response will thus be penalized by exposure to a painful stimulus (extinction effect). The means for producing an aversive, non-painful condition can be activated in the escape chamber, while the other chamber has only the means for producing a painful condition activated. The aversive, non-painful condition (e.g., light) discourages avoidance. However, escape will occur when the behavior driving force from the painful condition (e.g., heat or cold) overcomes the opposing driving force from the aversive, non-painful condition (e.g., light).

In a specific embodiment, a pain test (e.g., using thermally modulated floors as a driving force) can be followed by a test where light alone is the driving force (control test). The response to be measured from the test animal can be, for example, movement between two chambers, or activation of an escape response exhibiting means (e.g., pulling a lever, pressing a button, etc.).

A place preference test is also preferably conducted, which differs from the escape test by measuring the relative amount of time spent in the two chambers 12, 14 during each trial instead of the latency of the first crossing event between chambers. Higher pain sensitivity is inferred when the place preference is biased toward the chamber or chambers where the means for producing a painful condition is not activated (e.g., the thermally neutral chamber) and, optionally, the means for producing an aversive, non-painful condition is activated. Conversely, the test animal 10 is inferred to have lower pain sensitivity when it is willing to spend more time (and does spend more time) in the chamber or chambers where the means for producing a painful condition is activated (e.g., the chamber or chambers with the hot floor). A shift in place preference (this test's response time) can be used to infer a change in pain sensitivity, e.g., due to drug effects and/or disease state. In most experiments, the means for producing the aversive, non-painful condition will be activated in the chamber where the means for producing the painful condition is not activated (e.g., the thermally neutral chamber will be brightly lit). However, this is not a requirement.

A test of general motivation and motor ability can be conducted with the place-preference test, as well, where the means for producing a painful condition are not activated in the chambers (e.g., the floors of the chambers are a neutral, non-aversive temperature) and only the means for producing an aversive, non-painful condition (e.g., light) are used as an aversive force. A pain-relieving effect of a drug or other intervention can be inferred when the place preference (the environment the animal spends relatively more time in) in the pain sensitivity test shifts toward the chamber or chambers where the means for producing a painful condition was activated (e.g., the hot chamber), but remains unchanged when only the means for producing an aversive, non-painful condition (e.g., light) are used as the aversive force (the control test). The apparatus of the subject invention is particularly suited to perform these tests because it uses a conscious response to infer pain (not a reflex). This is important because withdrawal reflexes and conscious perception of pain do not always go hand in hand. The control test for motor deficits or general motivational depression uses the same motor task as the test using the painful stimulus and thus is a well-matched and valid control.

Generally, the test animal 30 is trained to escape thermal stimulation by first acclimating it to the apparatus, with the chamber floors at a neutral temperature (e.g., 39° C.). A few trials at about 45° C. will allow the animal to learn the position of the passageway 16 relative to the chambers 12, 14.

Each trial of most testing sessions will begin with the introduction of the animal into the apparatus. The test animal 30 can be introduced into the apparatus 10 by placing the test animal 30 in one of the chambers or, for example, by permitting the test animal 30 to enter one of the chambers through a door (e.g., guillotine door) that can be built into one or both of the chambers 12, 14. The means for producing an aversive, non-painful condition can be activated in both chambers before or after the test animal 30 is introduced into the apparatus 10. The choice of the trial duration depends on the needs of an experiment and, where the means for producing a painful condition are means for independently heating and cooling the floors of the chambers, the temperature of the floor can also be a determinant. Experiments using short acting drugs can require brief trial durations. However, continuous drug infusion can be conducted by means of continuous drug delivery devices, such as a flexible cannula, to which the test animal 30 can be tethered. After each trial, a timeout period can be granted (e.g., about 2 to about 4 minutes) where the means for producing a painful condition in the chambers are not activated. Subsequently, a new trial can be initiated by activating the means for producing a painful condition to a nociceptive level, in the chamber occupied by the test animal. A trial period can be about 8 minutes to about 12 minutes, particularly where means for independently heating and cooling the chamber floors are used and lower temperatures (about 43° C. to about 45° C.) are utilized. Where higher temperatures (about 47° C. to about 49° C.), a shorter trial period from about 1 minute to about 3 minutes is preferred.

Shown below in Table 1 is a non-painful exhaustive list of some specific features that may be utilized with the apparatus and methods of the subject invention.

TABLE 1

| | |
|---|---|
| Painful stimuli and means for presentation | Heat or cold delivered to the test animal through contact with a chamber floor<br>Heat or cold delivered through a Peltier device or heating element attached to or implanted within the test animal<br>Electrical stimulus through tether or wireless transmission to the peripheral nervous system or the central nervous system of the test animal<br>Chemical stimulus delivered to peripheral tissues or the peripheral or central nervous system<br>Mechanical stimulus (e.g., rectal distention through balloon inflation to induce visceral pain) through a tether or wirelessly controlled implant system |
| Non-painful stimuli and means for presentation to the test animal | Bright light within chamber (aversive stimulus)<br>Climate manipulation (heat or cold) in chamber (aversive or appetitive stimulus)<br>Electrical, thermal, or chemical stimuli administered to neural or non-neural tissues (aversive, effectively neutral, or appetitive) |
| Methods of measuring behavioral responses from the test animal | Tracking of movement between chambers<br>Measuring and comparing time spent in each chamber<br>Recording time and frequency of lever presses |
| Methods for measuring biological responses of the test animal | Sensing and recording physiological variables (e.g., electrical, temperature, pressure, chemical) through a tether or wireless telemetry (e.g., from the test animal's body surface, deep tissues, central nervous system) |
| Programmable contingencies between stimuli and responses | The test animal learns that its response will change the stimulus in a particular way |
| Modular design to accomodate specific research needs | |
| Hardware modules | One or more chambers<br>Position sensing system<br>Thermally controlled floor<br>Chamber illumination system<br>Climate control for chamber<br>Tether system<br>Data acquisition boards (digital I/O, analog (A) to digital (D) and D to A)<br>Signal conditioning hardware (rack modules) |
| Software modules (provided as source code to facilitate the development of custom software by the operator) | Control for water circulator (e.g., heat sink)<br>Temperature control for Peltier-based thermal floor-based, or tether-based, thermal probes<br>Position detection system<br>Processing modules for tether-based signals (analog and digital)<br>Software modules for common experimental needs (can be provided as fully functional applications)<br>Standard pain test, based upon the test animal's movement between chambers and a control test using bright light (this software can include routines for training the animals to a particular test) |

EXAMPLE 3

Operant Test Apparatus with Single Chamber

In another embodiment, the apparatus of the subject invention includes a single chamber, a means for presenting a painful stimulus to the test animal, a means for presenting an aversive, non-painful stimulus to the test animal, and a means for exhibiting an escape response, a means for implementing an appetitive stimulus, or both a means for exhibiting an escape response and a means for implementing an appetitive stimulus. The escape response exhibiting means can be a lever, button, switch, or other actuating mechanism that the test animal can activate or otherwise interact with to trigger termination or lessening of a painful stimulus or aversive, non-painful stimulus, thereby exhibiting a conscious escape response. The appetitive stimulus implementing means can be a lever, button, switch, or other activating mechanism that the test animal can activate or otherwise interact with in order to trigger an appetitive stimulus. The appetitive stimulus can be termination or lessening of a painful stimulus or aversive non-painful stimulus, or the appetitive stimulus can be a pleasurable sensation. If the apparatus includes an appetitive stimulus implementing means, the apparatus can include a means for presenting the appetitive stimulus. The appetitive stimulus presenting means can include, for example, a tether system or wireless system that delivers an appetitive agent (e.g., a drug) or otherwise stimulates pleasure centers of the test animal's nervous system. For example, the apparatus can include a lever that is in operable communication with a means for presenting a painful, aversive non-painful, appetitive, or addictive stimulus. Activation of the lever can have a variable effect. For example, the lever's effect can be contingent upon conditions within the chamber, such as light intensity or floor temperature.

A single chamber embodiment of the invention can be utilized to conduct an experiment to measure the ability of the animal to discriminate between conditions that may be subtly different. For example, the test animal can be trained to press the lever when it senses a certain condition. Correct identification of the condition would be rewarded, e.g., through an appetitive signal through a tether.

This embodiment is particularly advantageous if an extensive tether system is to be utilized in order to gather biological information from the test animal and/or to provide stimulus directly to the test animal. Although the painful stimulus and aversive non-painful stimulus can be selected from among the repertoire available with respect to the multiple chamber system, preferably, the means for presenting a painful stimulus to the test animal is a wireless system or tether system for delivering the painful stimulus to the test animal. The means for presenting an aversive non-painful stimulus can be a tether system or wireless system for delivering the aversive non-painful stimulus to the test animal. Alternatively, the means for presenting an aversive non-painful stimulus is a means for producing an aversive non-painful condition within the chamber.

It should be pointed out that the use of a single chamber does not preclude the use of a means for producing an aversive condition within the chamber, such as an aversive light source. For example, a lever can be programmed and operably linked with heating and/or cooling means in the floor of the chamber to reduce the heat of the chamber floor while simultaneously turning on an aversive light source. The test animal will then learn that the choice before it is either to tolerate the hot floor or the bright light.

It should be understood that the features and descriptions of features presented with respect to single chamber embodiments of the subject invention are non-painful exhaustive. The features described with respect to those embodiments of the apparatus having two or more chambers are to be considered equally applicable to the single chamber embodiments to the extent they are not inconsistent.

What is claimed is:

1. An apparatus for testing pain sensitivity in a test animal, comprising:

a first chamber;

a second chamber;

means for presenting a painful stimulus to a test animal when the test animal is within said first chamber or said second chamber, wherein said means for presenting a painful stimulus can rapidly present and rapidly remove a painful stimulus to the test animal;

means for presenting an aversive, non-painful stimulus to the test animal when the test animal is within said first chamber, wherein said means for presenting an aversive, non-painful stimulus can rapidly present and rapidly remove an aversive, non-painful stimulus to the test animal;

wherein said second chamber is connected to said first chamber by a passageway of sufficient size to permit the test animal to pass between said first and second chambers; and wherein said means for presenting a painful stimulus to the test animal when the test animal is within said first chamber and said means for presenting an aversive, non-painful stimulus to the test animal when the test animal is within said first chamber can each motivate the test animal to exhibit a conscious escape response;

means for presenting a painful stimulus to the test animal when the test animal is within said second chamber, wherein said means for presenting a painful stimulus to the test animal when the test animal is within said second chamber can rapidly present and rapidly remove a painful stimulus to the test animal; and means for presenting an aversive, non-painful stimulus to the test animal when the test animal is within said second chamber, wherein said means for presenting an aversive, non-painful stimulus to the test animal when the test animal is within said second chamber can rapidly present and rapidly remove an aversive, non-painful stimulus to the test animal; and wherein said means for presenting a painful stimulus to the test animal when the test animal is within the second chamber and said means for presenting an aversive, non-painful stimulus to the test animal when the test animal is within said second chamber can each motivate the test animal to exhibit a conscious escape response.

2. The apparatus of claim 1, wherein the conscious escape response exhibited by the test animal when the test animal is within said first chamber comprises the test animal moving from said first chamber through said passageway to second chamber.

3. The apparatus of claim 1, wherein the conscious escape response exhibited by the test animal when the test animal is within said second chamber comprises the test animal moving from said second chamber through said passageway to said first chamber.

4. The apparatus of claim 1, wherein the conscious escape response exhibited by the test animal when the test animal is within said first chamber comprises the test animal moving from said first chamber through said passageway to said second chamber, and wherein the conscious escape response exhibited by the test animal when the test animal is within said second chamber comprises the test animal moving from said second chamber through said passageway to said first chamber.

5. The apparatus of claim 1, wherein a painful stimulus can be presented to the test animal when the test animal is within each of said first and second chambers in about 30 seconds or less, wherein an aversive, non-painful stimulus can be presented to the test animal when the test animal is within each of said first and second chambers in about 30 seconds or less, wherein a painful stimulus can be removed when the test animal is within each of said first and second chambers in about 30 seconds or less, and wherein an aversive, non-painful stimulus can be removed when the test animal is within each of said first and second chambers in about 30 seconds or less.

6. The apparatus of claim 1, wherein a painful stimulus can be presented to the test animal when the test animal is within each of said first and second chambers in about 10 seconds or less, wherein an aversive, non-painful stimulus can be presented to the test animal when the test animal is within each of said first and second chambers in about 10 seconds or less, wherein a painful stimulus can be removed when the test animal is within each of said first and second chambers in about 10 seconds or less, and wherein an aversive, non-painful stimulus can be removed when the test animal is within each of said first and second chambers in about 10 seconds or less.

7. The apparatus of claim 1, wherein a painful stimulus can be presented to the test animal when the test animal is within each of said first and second chambers in about 5 seconds or less, wherein an aversive, non-painful stimulus can be presented to the test animal when the test animal is within each of said first and second chambers in about 5 seconds or less, wherein a painful stimulus can be removed when the test animal is within each of said first and second chambers in about 5 seconds or less, and wherein an aversive, non-painful stimulus can be removed when the test animal is within each of said first and second chambers in about 5 seconds or less.

8. The apparatus of claim 1, wherein said means for presenting a painful stimulus to the test animal presents the painful stimulus to the test animal directly through a link, wherein said link comprises a tether system or a wireless system.

9. The apparatus of claim 8, wherein said tether system or wireless system transmits a signal to the test animal, wherein said signal is selected from the group consisting of electrical stimuli, pharmacological stimuli, optical signals transmitted to optically sensitive physiological structures within the test animal, taste signals transmitted directly to the oral cavity of the test animal, olfactory signals transmitted directly to the nasal cavity of the test animal, and thermal signals transmitted to the test animal by a heat delivering device that is attached to the test animal or implanted within the test animal.

10. The apparatus of claim 1, wherein said means for presenting an aversive, non-painful stimulus to the test animal presents the aversive, non-painful stimulus to the test animal directly through a link, wherein said link comprises a tether system or a wireless system.

11. The apparatus of claim 10, wherein said tether system or wireless system transmits a signal to the test animal, wherein said signal is selected from the group consisting of electrical stimuli, pharmacological stimuli, optical signals transmitted to optically sensitive physiological structures within the test animal, taste signals transmitted directly to the oral cavity of the test animal, olfactory signals transmitted directly to the nasal cavity of the test animal, and thermal signals transmitted to the test animal by a heat delivering device that is attached to the test animal or implanted within the test animal.

12. The apparatus of claim 1, wherein said means for presenting a painful stimulus to the test animal comprises a means for producing a painful condition within each of said first chamber and said second chamber.

13. The apparatus of claim 12, wherein said means for producing a painful condition within each of said first chamber and said second chamber comprises a means for modulating the temperature of the air within each of said first chamber and said second chamber.

14. The apparatus of claim 1, wherein said means for presenting an aversive, non-painful stimulus to the test animal comprises a means for producing an aversive, non-painful condition within each of said first chamber and said second chamber.

15. The apparatus of claim 14, wherein said means for producing an aversive, non-painful condition in said first chamber comprises one or more light sources for lighting said first chamber, and wherein said means for producing an aversive, non-painful condition in said second chamber comprises one or more light sources for lighting said second chamber.

16. The apparatus of claim 15, wherein said first chamber has one or more walls, wherein said second chamber has one or more walls, wherein said one or more light sources for lighting said first chamber are located on or within one or more walls of said first chamber, and wherein said one or more light sources for lighting said second chamber are located on or within one or more walls of said second chamber.

17. The apparatus of claim 1, wherein said means for presenting a painful stimulus to the test animal comprises a means for producing a painful condition within each of said first chamber and said second chamber, and wherein said means for presenting an aversive, non-painful stimulus to the test animal comprises a means for producing an aversive, non-painful condition within each of said first chamber and said second chamber.

18. The apparatus of claim 17, wherein said first and second chambers each have a floor for supporting the test animal, wherein said first and second chamber floors are composed of a thermally conductive material, wherein said means for producing a painful condition in said first chamber comprises a means for independently heating and cooling said first chamber floor to temperatures that are painful to the test animal, and wherein said means for producing a painful condition in said second chamber comprises a means for independently heating and cooling said second chamber floor to temperatures that are painful to the test animal.

19. The apparatus of claim 18, wherein said means for independently heating and cooling said first and second chamber floors are capable of independently modulating the temperature of said first and second chamber floors, respectively, about 10° C. in about ten seconds or less, within a temperature range of about 0° C. to about 60° C.

20. The apparatus of claim 18, wherein said means for independently heating and cooling said first and second chamber floors are capable of independently modulating the temperature of said first and second chamber floors, respectively, about 10° C. in about five seconds or less, within a temperature range of about 0° C. to about 60° C.

21. The apparatus of claim 18, wherein said means for independently heating and cooling said first chamber floor comprises one or more thermoelectric modules located beneath said first chamber floor, and wherein said means for independently heating and cooling said second chamber floor comprises one or more thermoelectric modules located beneath said second chamber floor.

22. The apparatus of claim 21, wherein means for independently heating and cooling said first chamber floor further comprises a heat sink located beneath said one or more thermoelectric modules beneath said first chamber floor, and wherein said means for independently heating and cooling said second chamber floor further comprises a heat sink located beneath said one or more thermoelectric modules beneath said second chamber floor.

23. The apparatus of claim 22, wherein said thermally conductive material is copper and wherein said heat sinks are aluminum fluid-type heat sinks containing channels for fluid circulation.

24. The apparatus of claim 18, wherein said means for independently heating and cooling said first and second chambers are in operable communication with a temperature control device.

25. The apparatus of claim 1, further comprising means for sensing the passage of the animal through said passageway.

26. The apparatus of claims 25, wherein said sensing means comprises one or more infrared beam emitters and detectors operably positioned at said passageway, wherein said one or more infrared beam emitters and detectors produce one or more infrared beams, and wherein interruption of said one or more infrared beams by the test animal produces a signal indicating that the test animal has passed through said passageway.

27. The apparatus of claim 1, further comprising means for sensing the presence of the test animal within said first chamber and means for sensing the presence of the test animal within said second chamber.

28. The apparatus of claim 27, wherein said means for sensing the presence of the test animal within said first chamber comprises one or more infrared beam emitters and detectors operably positioned within said first chamber, wherein said means for sensing the presence of the test animal within said second chamber comprises one or more infrared beam emitters and detectors operably positioned within said second chamber, thereby producing one or more infrared beams within each of said first and second chambers, wherein interruption of said one or more infrared beams in said first chamber produces a signal indicating the presence of the test animal within said first chamber, and wherein interruption of said one or more infrared beams in said second chamber produces a signal indicating the presence of the test animal within said second chamber.

29. The apparatus of claim 28, wherein said apparatus further comprises means for measuring the amount of time the test animal is present in said first chamber and said second chamber.

30. The apparatus of claim 28, wherein said apparatus further comprises means for automating said means for presenting an aversive, non-painful stimulus to the test animal when the test animal is within said first chamber in response to said means for sensing the presence of the test animal within said first chamber, and means for automating said means for presenting an aversive, non-painful stimulus to the test animal when the test animal is within said second chamber in response to said means for sensing the presence of the test animal within said second chamber, wherein when the test animal passes through said passageway from said first chamber to said second chamber, said means for presenting an aversive, non-painful condition to the test animal when the test animal is within said second chamber is automatically activated or automatically deactivated, and wherein when the test animal passes through said passageway from said second chamber to said first chamber, the means for presenting an aversive, non-painful stimulus to the test animal when the test animal is within said first chamber is automatically activated or automatically deactivated.

31. The apparatus of claim 28, wherein said apparatus further comprises means for automating said means for presenting a painful stimulus to the test animal when the test animal is within said first chamber in response to said means for sensing the presence of the test animal within said first chamber, and means for automating said means for presenting a painful stimulus to the test animal when the test animal is within said second chamber in response to said means for sensing the presence of the test animal within said second chamber, wherein when the test animal passes through said passageway from said first chamber to said second chamber, said means for presenting a painful stimulus to the test animal when the test animal is within said second chamber is automatically activated or automatically deactivated, and wherein when the test animal passes through said passageway from said second chamber to said first chamber, said means for presenting a painful stimulus to the test animal when the test animal is within said first chamber is automatically activated or automatically deactivated.

32. The apparatus of claim 1, wherein the shape and dimensions of said first chamber and said second chamber are substantially identical.

33. The apparatus of claim 1, further comprising a tether system for obtaining biological information from the test animal when the test animal is within said apparatus.

34. The apparatus of claim 33, wherein said tether system comprises a means for obtaining a biological sample from the test animal when the test animal is within said apparatus.

35. The apparatus of claim 1, further comprising a wireless system for obtaining biological information from the test animal when the test animal is within said apparatus.

36. The apparatus of claim 35, wherein said wireless system is selected from the group consisting of radio-electric transmission systems, optical transmission systems, and ultrasound transmission systems.

37. The apparatus of claim 1, further comprising a means for exhibiting a conscious escape response within said first chamber, within said second chamber, or within each of said first and second chambers, wherein when said conscious escape response exhibiting means is activated by the test animal, the painful stimulus or the aversive, non-painful stimulus is terminated or lessened in magnitude.

38. The apparatus of claim 37, wherein said conscious escape response exhibiting means is selected from the group consisting of a lever, button, and switch.

39. The apparatus of claim 37, wherein the conscious escape response exhibited by the test animal when the test animal is within said first chamber comprises the test animal activating said escape response exhibiting means within said first chamber.

40. The apparatus of claim 37, wherein the conscious escape response exhibited by the test animal when the test animal is within said second chamber comprises the test animal activating said escape response exhibiting means within said second chamber.

41. The apparatus of claim 37, wherein the conscious escape response exhibited by the test animal when the test animal is within said first chamber comprises the test animal activating said escape response exhibiting means within said first chamber, and wherein the conscious escape response exhibited by the test animal when the test animal is within said second chamber comprises the test animal activating said escape response exhibiting means within said second chamber.

42. The apparatus of claim 1, further comprising a means for implementing an appetitive stimulus to the test animal within said first chamber, within said second chamber, or within each of said first and second chambers, wherein when said means for implementing an appetitive stimulus to the test animal is activated by the test animal, an appetitive stimulus is presented to the test animal.

43. The apparatus of claim 42, wherein said appetitive stimulus implementing means is selected from the group consisting of a lever, button, and switch.

44. The apparatus of claim 42, further comprising a means for presenting an appetitive stimulus to the test animal when the test animal is within said first chamber or said second chamber.

45. The apparatus of claim 1, further comprising one or more additional chambers connected to said first chamber, connected to said second chamber, or connected to both said first and second chambers.

46. A method for testing the pain sensitivity of a test animal, comprising the steps of:
   introducing the test animal into an apparatus comprising a first chamber and a second chamber, wherein said chambers are connected by a passageway;
   presenting an aversive, non-painful stimulus in said first chamber;
   presenting a painful stimulus in said second chamber when said second chamber is occupied by the test animal, thereby motivating the test animal to exhibit a conscious escape response if the test animal perceives pain; and
   measuring the escape latency exhibited by the test animal.

47. The method according to claim 46, wherein the conscious escape response comprises the test animal moving from said second chamber to said first chamber, and wherein the test animal is thereby presented with the aversive non-painful stimulus in said first chamber.

48. The method according to claim 47, wherein said escape latency is the amount of time the test animal spends in said second chamber after the painful stimulus is presented in said second chamber.

49. The method according to claim 47, further comprising comparing said escape latency with a control escape latency.

50. The method according to claim 47, wherein the test animal has undergone a treatment to be evaluated for its effect on the test animal's pain sensitivity.

51. The method according to claim 50, wherein the treatment is selected from the group consisting of administration of a substance, surgical procedure, and genetic manipulation.

52. The method according to claim 47, wherein the test animal is administered a substance to be evaluated for its effect on the test animal's pain sensitivity.

53. The method according to claim 47, wherein before, during, or after the test animal is introduced into said apparatus, the test animal is administered a substance to be tested for its effect on the test animal's pain sensitivity.

54. The method according to claim 47, wherein the test animal suffers from a disease or other pathological condition.

55. A method for testing the pain sensitivity of a test animal, comprising the steps of:
   introducing the test animal into the apparatus of claim 1;
   activating said means for presenting an aversive, non-painful stimulus in said first chamber;
   activating said means for presenting a painful stimulus in said second chamber when said second chamber is occupied by the test animal, thereby motivating the test animal to move through said passageway to said first chamber if the test animal perceives pain; and
   measuring the escape latency exhibited by the test animal.

56. The method according to claim 55, wherein said escape latency is the amount of time the test animal spends in said second chamber after said means for presenting a painful stimulus is activated in said second chamber.

57. The method according to claim 55, further comprising comparing said escape latency with a control escape latency.

58. The method according to claim 57, wherein said control escape latency is exhibited by the test animal when the test animal is introduced in the apparatus of claim 1, said means for presenting a painful stimulus in said first chamber is not activated, said means for presenting a painful stimulus in said second chamber is not activated, said means for presenting an aversive, non-painful stimulus in said first chamber is activated if said first chamber is occupied by the test animal, thereby motivating the test animal to move through said passageway to said second chamber, and said means for presenting an aversive, non-painful stimulus in said second chamber is activated if said second chamber is occupied by the test animal, thereby causing the test animal to move through said passageway to said first chamber.

59. The method according to claim 58, wherein pain sensitivity in the test animal can be inferred if the escape latency is lower than that of the control escape latency.

60. The method according to claim 55, wherein said first and second chambers each have a floor for supporting the test animal, wherein said first and second chamber floors are each composed of a thermally conductive material, wherein said means for producing a painful condition in said first chamber comprises a means for independently heating and cooling said first chamber floor to temperatures that are painful to the test animal, and wherein said means for producing a painful condition in said second chamber comprises means for independently heating and cooling said second chamber floor to temperatures that are painful to the test animal.

61. The method according to claim 60, wherein said means for independently heating and cooling said first chamber floor comprises one or more thermoelectric modules located beneath said first chamber floor, and wherein said means for independently heating and cooling said second chamber floor comprises one or more thermoelectric modules located beneath said second chamber floor.

62. The method according to claim 61, wherein said means for independently heating and cooling said first chamber floor further comprises a heat sink located beneath said one or more thermoelectric modules beneath said first chamber floor, and wherein said means for independently heating and cooling said second chamber floor further comprises a heat sink located beneath said one or more thermoelectric modules beneath said second chamber floor.

63. The method according to claim 55, wherein said apparatus further comprises means for sensing the presence of the test animal within said first chamber and means for sensing the presence of the test animal within said second chamber.

64. The method according to claim 63, wherein said means for sensing the presence of the test animal within said first chamber comprises one or more infrared beam emitters and detectors operably positioned within said first chamber, wherein said means for sensing the presence of the test animal within said second chamber comprises one or more infrared beam emitters and detectors operably positioned within said second chamber, thereby producing one or more infrared beams within each of said first and second chambers, wherein interruption of said one or more infrared beams in said first chamber produces a signal indicating the presence of the test animal within said first chamber, and wherein interruption of said one or more infrared beams in said second chamber produces a signal indicating the presence of the test animal within said second chamber.

65. A method for determining pain sensitivity in a test animal, comprising the steps of:
   introducing the test animal into the apparatus of claim 1;
   activating said means for presenting an aversive, non-painful stimulus in said first chamber;
   activating said means for presenting a painful stimulus in said second chamber when said second chamber is occupied by the test animal, thereby motivating the test animal to move through said passageway to said first chamber;

deactivating said means for presenting an aversive, non-painful stimulus in said first chamber;

deactivating said means for presenting a painful stimulus in said second chamber;

activating said means for presenting an aversive, non-painful stimulus in either said first chamber or said second chamber;

activating said means for presenting a painful stimulus in whichever of said first and second chambers is occupied by the test animal, thereby motivating the test animal to move through said passageway to the opposite chamber; and measuring the place preference exhibited by the test animal.

66. The method according to claim 65, wherein the place preference is the environment the test animal spends more time in, wherein the environment is selected from the group consisting of:

said first chamber, when said means for presenting an aversive, non-painful stimulus is activated in said first chamber; said second chamber, when said means for presenting an aversive, non-painful stimulus is activated in said second chamber; or both said first chamber and said second chamber, when both said means for presenting an aversive, non-painful stimulus in said first chamber and said second chamber are activated; and said first chamber, when said means for presenting a painful stimulus is activated in said first chamber; said second chamber, when said means for presenting a painful stimulus is activated in said second chamber; or both said first chamber and said second chamber, when both said means for presenting a painful stimulus in said first chamber and said second chamber are activated, respectively.

67. The method according to claim 65, wherein pain sensitivity is inferred if the test animal spends more time in:

said first chamber, when said means for presenting a painful stimulus in said first chamber is deactivated and said means for presenting an aversive non-painful stimulus in said first chamber is activated;

said second chamber, when said means for presenting a painful stimulus in said second chamber is deactivated and said means for presenting an aversive, non-painful stimulus in said second chamber is activated; or both said first chamber and said second chamber, when both said means for presenting a painful stimulus in said first chamber and said second chamber are deactivated and both said means for presenting an aversive, non-painful stimulus in said first chambers and said second chamber are activated, respectively.

68. The method according to claim 65, wherein said means for presenting a painful stimulus to the test animal comprises a means for producing a painful condition within each of said first chamber and said second chamber.

69. The method according to claim 65, wherein said means for presenting an aversive, non-painful stimulus to the test animal comprises a means producing an aversive, non-painful condition within each of said first chamber and said second chamber.

70. The method according to claim 65, wherein said means for presenting a painful stimulus to the test animal comprises a means for producing a painful condition within each of said first chamber and said second chamber, and wherein said means for presenting an aversive, non-painful stimulus to the test animal comprises producing an aversive, non-painful condition within each of said first chamber and said second chamber.

71. The method, according to claim 65, wherein said first and second chambers each have a floor for supporting the test animal, wherein said first and second chamber floors are each composed of a thermally conductive material, wherein said means for presenting a painful stimulus in said first chamber comprises a means for independently heating and cooling said first chamber floor to temperatures that are painful to the test animal, and wherein said means for producing a painful condition in said second chamber comprises means for independently heating and cooling said second chamber floor to temperatures that are painful to the test animal.

72. The method according to claim 71, wherein said means for independently heating and cooling said first chamber floor comprises one or more thermoelectric modules located beneath said first chamber floor, and wherein said means for independently heating and cooling said second chamber floor comprises one or more thermoelectric modules located beneath said second chamber floor.

73. The method according to claim 72, wherein said means for independently heating and cooling said first chamber floor further comprises a heat sink located beneath said one or more thermoelectric modules beneath said first chamber floor, and wherein said means for independently heating and cooling said second chamber floor further comprises a heat sink located beneath said one or more thermoelectric modules beneath said second chamber floor.

74. The method according to claim 65, wherein said apparatus further comprises means for sensing the presence of the test animal within said first chamber and means for sensing the presence of the test animal within said second chamber.

75. The method according to claim 74, wherein said means for sensing the presence of the test animal within said first chamber comprises one or more infrared beam emitters and detectors operably positioned within said first chamber, wherein said means for sensing the presence of the test animal within said second chamber comprises one or more infrared beam emitters and detectors operably positioned within said second chamber, thereby producing one or more infrared beams within each of said first and second chambers, wherein interruption of said one or more infrared beams in said first chamber produces a signal indicating the presence of the test animal within said first chamber, and wherein interruption of said one or more infrared beams in said second chamber produces a signal indicating the presence of the test animal within said second chamber.

76. An apparatus for testing pain sensitivity in a test animal, comprising:

a chamber;

means for presenting a painful stimulus to a test animal when the test animal is within said chamber;

means for presenting an aversive, non-painful stimulus to the test animal when the test animal is within said chamber; and means for exhibiting a conscious escape response when the test animal is within said chamber, wherein when said conscious escape response exhibiting means is activated by the test animal, the painful stimulus or the aversive, non-painful stimulus is terminated or lessened in magnitude.

77. The apparatus of claim 76, wherein said conscious escape response exhibiting means is selected from the group consisting of a lever, button, and switch.

78. An apparatus for testing pain sensitivity in a test animal, comprising:
- a chamber;
- means for presenting a painful stimulus to a test animal when the test animal is within said chamber;
- means for presenting an aversive, non-painful stimulus to the test animal when the test animal is within said chamber; and
- means for implementing an appetitive stimulus to the test animal, wherein when said appetitive stimulus implementing means is activated by the test animal, an appetitive stimulus is presented to the test animal.

79. The apparatus of claim 78, wherein said appetitive stimulus is selected from the group consisting of termination of lessening of the painful stimulus, termination or lessening of the aversive non-painful stimulus, and an affirmative pleasurable stimulus.

80. The apparatus of claim 79, wherein said apparatus further comprises a means for presenting the appetitive stimulus to the test animal, wherein said appetitive stimulus is an affirmative pleasurable stimulus, and wherein said affirmative pleasurable stimulus comprises administration of a drug.

81. A method for testing the pain sensitivity of a test animal, comprising the steps of:
- introducing the test animal into the apparatus of claim 76; and
- measuring the escape latency exhibited by the test animal.

82. A method for testing the pain sensitivity of a test animal, comprising the steps of:
- introducing the test animal into the apparatus of claim 78; and
- measuring the escape latency exhibited by the test animal.

\* \* \* \* \*

UNITED STATES PATENT AND TRADEMARK OFFICE
CERTIFICATE OF CORRECTION

PATENT NO.   : 6,637,372 B2
DATED        : October 28, 2003
INVENTOR(S)  : Andre Paul Mauderli and Charles J. Vierck It is certified that error appears in the above-identified patent and that said Letters Patent is hereby corrected as shown below:

Column 3,
Line 6, "1983" should read -- 1983b --.

Column 15,
Line 9, "fourth 60" should read -- fourth wall 60 --.

Column 17,
Line 9, "fourth 60" should read -- fourth wall 60 --.

Signed and Sealed this

Twenty-fifth Day of May, 2004

JON W. DUDAS
*Acting Director of the United States Patent and Trademark Office*